United States Patent
Vizard et al.

(10) Patent No.: US 7,031,084 B2
(45) Date of Patent: Apr. 18, 2006

(54) IMAGING SYSTEM USING COMBINED DICHROIC/HIGH-PASS FILTERS

(75) Inventors: Douglas L. Vizard, Durham, CT (US); William E. Mclaughlin, Guilford, CT (US)

(73) Assignee: Eastman Kodak Company, Rochester, NY (US)

(*) Notice: Subject to any disclaimer, the term of this patent is extended or adjusted under 35 U.S.C. 154(b) by 12 days.

(21) Appl. No.: 10/625,376

(22) Filed: Jul. 23, 2003

(65) Prior Publication Data

US 2005/0018332 A1 Jan. 27, 2005

(51) Int. Cl.
*G02B 5/22* (2006.01)

(52) U.S. Cl. .................. 359/885; 359/723; 356/417
(58) Field of Classification Search .............. 359/885, 359/890, 722, 723; 356/417
See application file for complete search history.

(56) References Cited

U.S. PATENT DOCUMENTS

| | | | |
|---|---|---|---|
| 3,449,945 A | 6/1969 | Mohrman | |
| 4,573,195 A | 2/1986 | de France | |
| 5,112,127 A * | 5/1992 | Carrabba et al. | 356/301 |
| 5,943,129 A * | 8/1999 | Hoyt et al. | 356/318 |
| 2003/0086608 A1 | 5/2003 | Frost et al. | |
| 2004/0075844 A1 * | 4/2004 | Marron et al. | 356/514 |

* cited by examiner

*Primary Examiner*—Leo Boutsikaris
(74) *Attorney, Agent, or Firm*—William F. Noval

(57) ABSTRACT

An imaging system including: a lens; a dichroic filter positioned in front of the lens; and a high pass filter positioned between the lens and the dichroic filter. An appropriate design coordinating the components of such an imaging system diminishes imaging artifacts related to wide-angle imaging of fluorescent objects.

3 Claims, 3 Drawing Sheets

TRANSMISSION SPECTRUM
FOR BANDPASS FILTER

IMAGING SYSTEM USING COMBINED DICHROIC/HIGH-PASS FILTERS

FIELD OF THE INVENTION

This invention relates in general to fluorescent imaging systems and more particularly to the suppression of stray wide angle excitation light passed by a dichroic filter.

BACKGROUND OF THE INVENTION

The most common rationale for the fluorescent measure is the need for sensitivity, or a high signal-to-noise level afforded by a dark-field measure of fluorescence. The main object of the fluorescent measure is to admit only the fluorescent signal (range of wavelengths) to a sensor, and to reject excitation wavelengths. Fluorescent measurement sensitivity is usually limited by the noise associated with a background of stray light that compromises the dark-field. Background stray light may emanate from a sample or the measurement system; stray light from the system is mitigated by spectral filtration. Spectral filtration of light is essential to fluorescent measurement, wherein stray light from excitation energy must be eliminated from an optical light path that directs the essential fluorescent energy signal to a photo sensor.

For many fluorescent applications, the greatest sensitivity is obtained by exciting with a wavelength of light that is only tens of nanometers below the emission wavelength, where the excitation/emission difference is called the Stokes Shift of the fluorochrome. Dichroic (interference) filters are commonly applied, since they can be designed and manufactured to enable the appropriate rejection of stray excitation light from productive emission light. While high-pass filters that absorb light with a chromaphore can be designed and manufactured to absorb excitation and pass emission, they generally do not enable productive rejection and transparency over the demanded tens of nanometers and absorbing chromaphores have a tendency to fluoresce (contribute noise in the domain measurement wavelengths). Further, the design/manufacture of a dichroic filter is amenable to enabling a bandpass of transmitted light, designated by a cut-on and cut-off wavelength of an emission spectrum (according to the conventional spectrum of increasing wavelength), providing a transmission window for the emission. The well-designed bandpass dichroic is essential to the sensitive fluorescent measure, since materials other than the fluorochrome targeted for measure may fluoresce. To the likely extent that those other materials fluoresce out of the bandpass designed for a targeted fluorochrome, their emissions are rejected the sensitivity of the fluorescent measure improves.

An increasingly common need for the fluorescent measure is the imaging applications, wherein a combination of lenses direct the fluorescent energy signal to an area sensor such as film or an electronic sensor (CCD array). To further the sensitivity and dynamic range of the fluorescent measurement, it is increasingly common to use a cooled CCD array sensor. To further the speed and acuity of the imaging, and to broaden the operating range of the optics, very sophisticated lenses (many elements) must be used.

A difficulty in applying an appropriately designed dichroic filter to the imaging application is that the dichroic filter bandpass is a function of the angle of incidence of light on the filter plane, as shown in FIG. 1A. Specifically, light incident at off-normal incidence traverses a longer optical distance in the interference coating; hence the cut-on (and cut-off) wavelength of the dichroic filter decrease, or the bandpass blue-shifts. Hence, for the wide-angle of view enabled by a sophisticated lens, the emission filter bandpass presents a blue-shift that increases with image radius (FIG. 1B). The radial-blue shift can cause a severe artifact in a high-sensitivity fluorescent imaging application if the blue-shifted cut-on of the emission filter significantly overlaps the cut-off of the excitation light. Consequent stray excitation light infiltrates the periphery of the field of view, producing imaging artifacts, often viewed as bright rings in the otherwise dark field. Generally, the bright ring artifacts are a reflection of the circular features in the multi-element lens that reflect the stray light back to the dichroic filter, which rejects the light back into the lens and ultimately to the sensor. An example of the imaging artifact is shown in FIG. 2A.

One method of managing blue-shifted bandpass in a wide-angle imaging system is the placement of a dichroic emitter filter behind the lens elements (shown in FIG. 1A as element—in dashed lines 100). The method is somewhat more effective at reducing blue shift, since the wide angle rays can be more suppressed in the well-designed lens. Although effective, the method fails to reject excessive excitation light from multiple lens elements having reflective and fluorescent materials and surfaces within the lens. A resulting image artifact appears as a haze (not necessarily uniform) in the dark field, which contributes to the background noise.

There is thus a need for a cost effective technique that suppresses imaging artifacts that impede sensitive fluorescent measures.

SUMMARY OF THE INVENTION

According to the present invention, there is provided a fulfillment of the needs and a solution to the problems discussed above.

According to a feature of the present invention, there is provided an imaging system comprising: a lens; a dichroic filter positioned in front of said lens; and a high pass filter positioned between said lens and said dichroic filter.

According to another feature of the present invention there is provided an imaging system comprising: a lens for imaging a fluorescent image on an electronic sensor; a dichroic bandpass filter positioned in front of said lens for passing the emission spectrum of the fluorescent image and for filtering out excitation light; and a high pass filter positioned between said lens and said dichroic filter for filtering any stray wide angle excitation light passed by said dichroic filter.

ADVANTAGEOUS EFFECT OF THE INVENTION

The invention has the following advantages.

1. An imaging system has a cost effective technique for suppressing imaging artifacts that impede sensitive fluorescent measures.
2. Blue-shifted bandpass of excitation light in a wide angle fluorescent imaging system is minimized.

DETAILED DESCRIPTION OF THE INVENTION

Figure 1A:
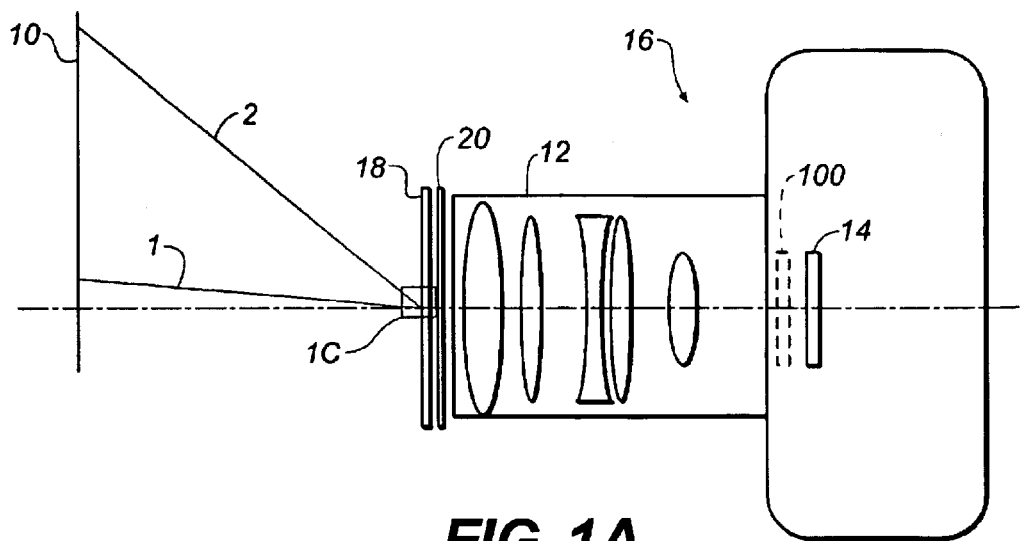
FIGS. 1A and 1C are diagrammatic views of an embodiment of the present invention.
Figure 1C:
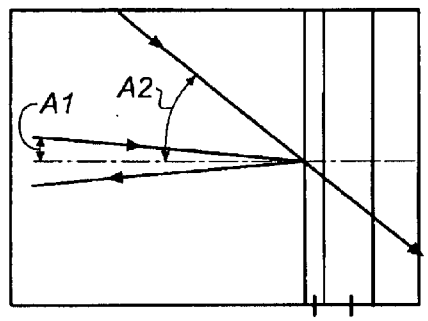
Figure 1B:
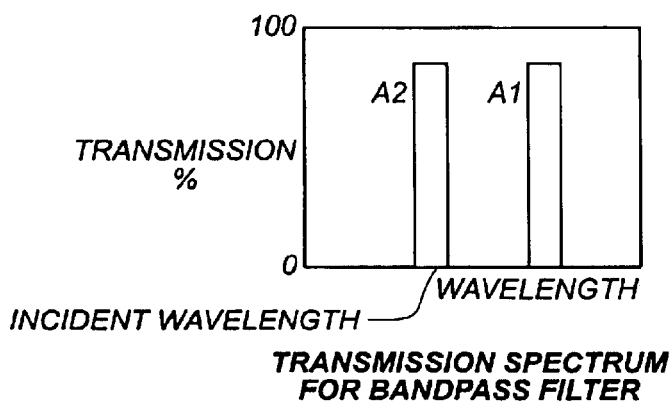
FIG. 1B is a graphical view of transmission vs. wavelength of a bandpass filter.

Referring now to FIGS. 1A through 1C, there is shown an embodiment of the present invention. As shown, an object plane 10 of a fluorescent image is imaged by wide angle lens 12 onto an electronic sensor 14 of imaging system 16.

Light rays of the same wavelength are incident on a dichroic bandpass filter 18 placed in front of the camera lens 12. Light ray 1 is incident at a narrow angle (A1) nearly normal to the filter surface, as shown in the blowup segment of the diagram. Light ray 2 is incident at wide angle, A2. The dichroic filter 18 is designed with a bandpass spectrum shown in the transmission spectrum of FIG. 1B. The designed filter 18 successfully rejects the rays of normal or narrow angle. A ray incident at a wide angle traverses a greater optical distance in the interference coating, having the effect of blue-shifting the bandpass spectrum. At a sufficiently wide angle of incidence (A2), a ray such as '2' will be passed by the filter 18. A well-designed high-pass filter (HP) 20 interposed between the dichroic filter 18 and the lens 12 will attenuate the wide-angle rays that would be normally rejected and at a narrow angle.

Figure 2B:
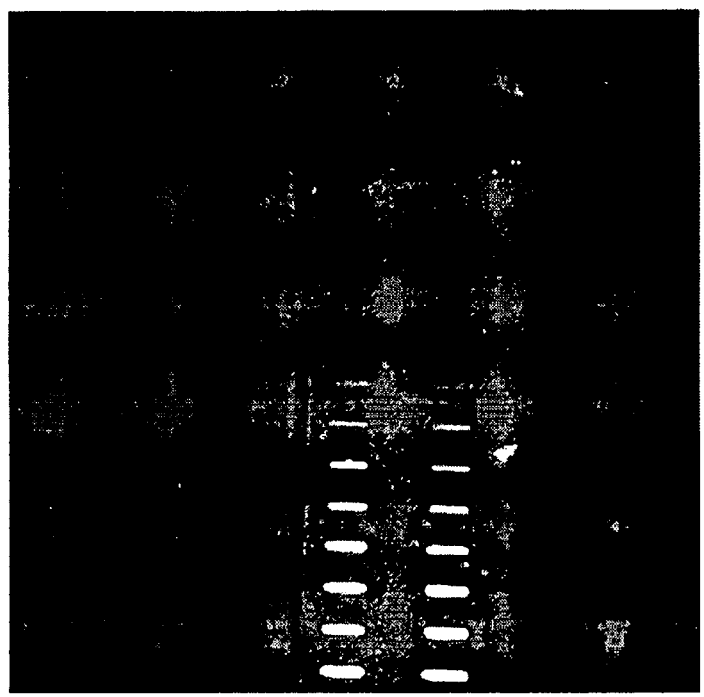
FIGS. 2A and 2B are diagrammatic views useful in explaining the present invention.
Figure 2A:
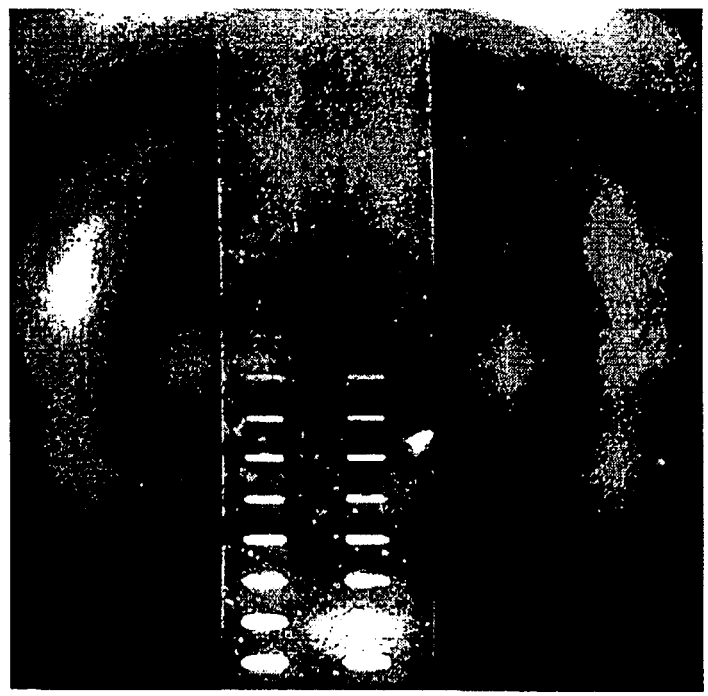

According to the present invention there is provided a cost effective technique that suppresses imaging artifacts that impede sensitive fluorescent measures. The principle feature of the invention imposes an inexpensive, high-pass absorbing filter 20 between the lens 12 face and a dichroic filter 18. The high-pass filter 20 is chosen to have sufficient absorbance at the cut-off wavelength of excitation to assure that stray excitation light is appropriately attenuated should it be passed by a blue-shifted emitter filter operating at a wide angle. An example of the effectiveness of the invention is apparent in the comparative images in FIGS. 2A and 2B, comparative wide-angle images from a sensitive fluorescent measurement system. The widest angle of view corresponds to about 21 degrees of normal incidence. The object measured is Cy5.5 dye in a band format absorbed into a nitrocellulose membrane. Circular image artifacts are present in FIG. 2A, using a dichroic filter only, and absent in FIG. 2B, in which an added adsorbing filter is applied. The imaging system used consists of a large TV lens (10× zoom), a 630 nm AF30 Omega exciter filtering a halogen light source, a 700 nm DF30 Omega emitter filter. The absorbing filter applied is a Wratten 70. The camera is a Kodak IS2000, and the presented image is an 8-bit slice (dark background through 256 levels) of the 16-bit digitized output.

Further understanding and design principles of the invention can be conveyed by analytical modeling. The point of the analysis is to estimate the overlap between excitation light and emission bandpass. The source of the blue-shift is incident angle, and is about 0.5 nm per degree of off-normal incidence as measured for high-quality dichroic filters. A wide-angle image system includes the light incident at 25 degrees or more off normal, resulting in an emitter cut-on blue shift of 13 nm. For the sensitive fluorescent assay, exciter-emitter filter pairs will be used that will be typically spaced about 60 nm apart in central wavelength, and each filter will have a 30–35 nm bandpass (FWHM, full width at half maximum). A high-quality dichroic bandpass filter having a 35 nm FWHM translates to greater than a 50 nm bandpass at 0.001 maximum (accumulated experimental data). For sensitive fluorescent assays, assurance of a $>10^{-6}$ suppression of excitation light in the emitter bandpass is essential, and is obtained by assuring a domain wavelength having >0.001 attenuation for both exciter cut-off and emitter cut-on. The graph in FIG. 3b shows that at a fractional transmission of 0.001, an approximate 5 nm domain exists between exciter cut-off and emitter cut-on for normal incidence. However, a 13 nm blue-shift in the emitter violates the criterion, implying that the widest angles of view will permit significant exciter light to pass through the emitter filter. Interposing an absorbing filter (modeled after a typical Wratten high-pass) having an OD of >2 at the 0.001 cut-off level of the exciter suffices to just meet the $10^{-6}$ criterion of attenuation.

It is important to use such analytical modeling steps in the design of the emitter/absorber combination filter. In practice, meeting the $10^{-6}$ attenuation sufficiency criterion is important, but must be treated as a critical optimum. Choosing much greater attenuation by the absorbing filter does attenuate productive fluorescent emission at normal incidence and does so increasingly as a function of image radius due to the radial blue-shift of the emitter dichroic. Further, any absorbing filter is liable to yield a fluorescent background if too much excitation light is absorbed. Hence, it is important to interpose an absorbing filter only between the dichroic and the lens face. The marked effectiveness of the absorbing filter to reduce the image artifact is amplified by the principle that the wide angle excitation light passed by the blue-shifted emitter must pass through the absorber no less than three times before it can participate in image formation. Hence, choosing a high-pass absorber having an OD of >1 at the 0.001 cut-off level of the exciter is deemed minimally sufficient. Choosing a high-pass absorber having an OD of <1 will certainly be sufficient for narrower fields of view.

Figure 3A:
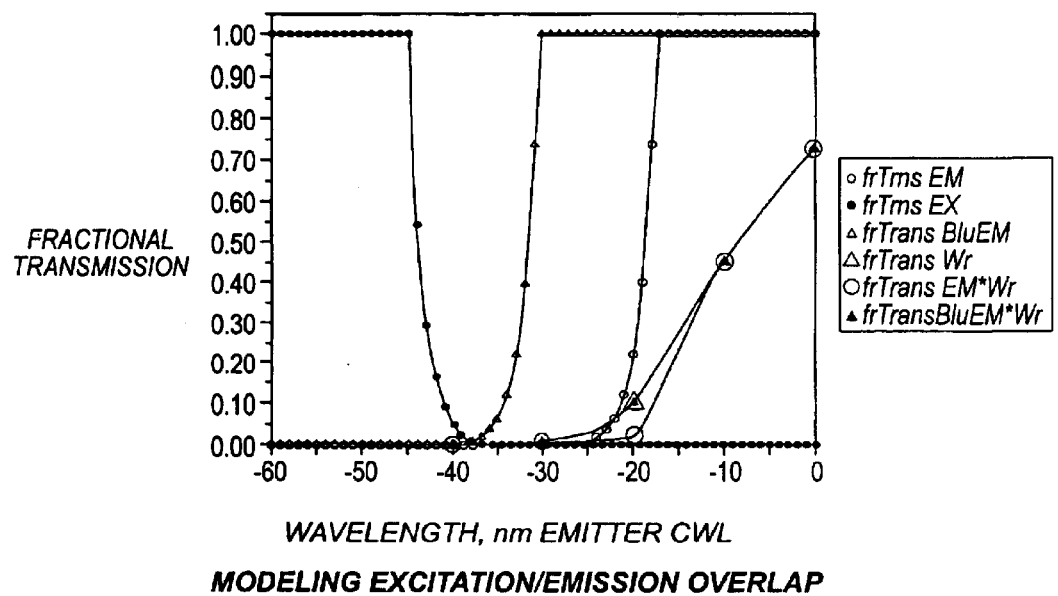
FIGS. 3a and 3b are graphical views showing excitation/emission wavelength overlap.
Figure 3B:
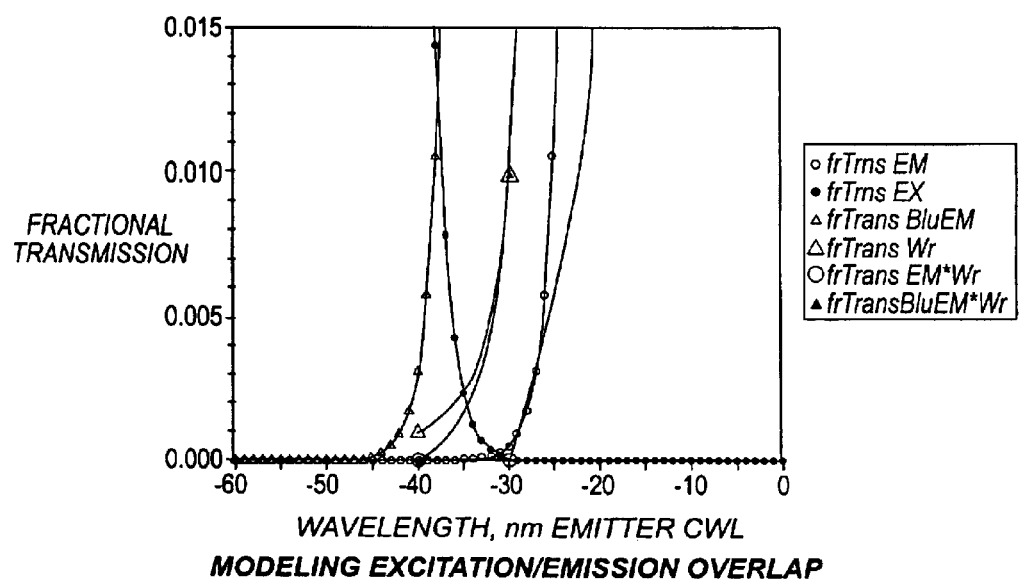

Referring to FIGS. 3a and 3b, there is shown a graphical presentation of fractional transmission as a function of wavelength for excitation and emission filters used for fluorescent measurement. The wavelength scale is given in nanometers from the central wavelength of the emitter filter. Exciter (EX) and emitter (EM) filter central wavelengths are displaced by 60 nm; the exciter filter is 30 nm FWHM and the emitter is 35 nm FWHM. The maximum transmission of exciter and emitter filters is about 0.8 fractional transmission in reality. The data presented is modeled according to experimental measures of filter properties. The high-pass absorbing filter represented is according to a typical Wratten filter. The right-hand graph is simply an expanded scale of the left, and demonstrates best the overlap between the exciter cut-off (frTransEX) and the blue-shifted emitter cut-on (frTransBluEM). At a transmission of 0.001, a gap of about 5 nm separates the exciter cut-off and the normal emitter cut-on (frTransEM). The absorbing filter has a fractional transmission of <0.01 at the 0.001 level of exciter cut-off, and is more than sufficient to suppress the relevant overlap represented by the product frTransBluEM*Wr.

In the case of the Kodak IS2000 device, this manifests as exciter light entering the lens, internal lens features reflecting back to dichroic face, the image of those lens features being rejected (reflected) by the dichroic, re-entering the lens to ultimately form an image of the internal lens features. Since most of the internal lens features are concentric circles (the IS2000 lens also has some irregular "posts"), the circular patterns (including posts) clearly show as serious artifacts to a dark-field that must be "flat" to enable appropriate analysis of sensitive fluorescent imaging.

A solution to this problem has been tested, and seems to work extremely well. A combination filter is constructed with an appropriately chosen high-pass Wratten filter contacted the back side (camera side) of the dichroic emitter. Excitation light bandpassed by angular blue-shifting of the emitter is attenuated by the Wratten, and the cross-talk modeling calculation shown in the lower graphs in the above demonstrate conformance to the 0.001 criteria for the combined filter. Experimentally, the dark field is nominally flat and absent of circular and other artifacts. The only effect that the combination filter does show is an enhanced, gradual vignetting, since the combination emitter filter has a diminishing band pass from center to edge, and the vignetting becomes increasingly apparent with a wider field of view.

The invention has been described in detail with particular reference to certain preferred embodiments thereof, but it will be understood that variations and modifications can be effected within the spirit and scope of the invention.

PARTS LIST 1 light ray
2 light ray
10 plane
12 camera lens
14 electronic sensor
16 imaging system
18 dichroic filter
20 high-pass absorbing filter
100 dichroic element

What is claimed is:

1. An imaging system comprising:

a wide-angle lens;

a dichroic filter positioned in front of said wide-angle lens, wherein said dichroic filter passes light of a first band of frequencies and successfully rejects light of a second band of frequencies which are incident on said wide-angle lens up to a narrow angle to normal to said wide-angle lens but wherein stray light of said second band of frequencies incident on said wide-angle lens at a wide angle to the normal of said wide-angle lens may be passed; and a high pass filter positioned between said lens and said dichroic filter, wherein said high pass filter rejects any said stray light which may have passed through said dichroic filter of said second band of frequencies incident at a wide-angle to the normal of said wide-angle lens.

2. An imaging system comprising:

a wide-angle lens for imaging a fluorescent image on an electronic sensor;

a dichroic bandpass filter positioned in front of said wide-angle lens for passing the emission spectrum of the fluorescent image and for successfully filtering out excitation light incident on said wide-angle lens up to a narrow angle to normal to said wide-angle lens, but wherein stray excitation light incident on said wide-angle lens at a wide angle to the normal of said wide-angle lens may be passed; and a high pass filter positioned between said wide-angle lens and said dichroic bandpass filter for filtering any said stray wide angle excitation light which may have been passed by said dichroic bandpass filter.

3. The imaging system of claim 2 wherein said high pass filter has an optical density greater than 1 at the nominal cut-off wavelength of the dichroic bandpass filter.

* * * * *